US006464976B1

United States Patent
LaFace et al.

(10) Patent No.: US 6,464,976 B1
(45) Date of Patent: Oct. 15, 2002

(54) METHODS AND COMPOSITIONS FOR REDUCING IMMUNE RESPONSE

(75) Inventors: Drake M. LaFace; Amena Rahman, both of San Diego; Paul W. Shabram, Olivenhain; Van T. Tsai, San Diego, all of CA (US)

(73) Assignee: Canji, Inc., San Diego, CA (US)

(*) Notice: Subject to any disclaimer, the term of this patent is extended or adjusted under 35 U.S.C. 154(b) by 0 days.

(21) Appl. No.: 09/653,474

(22) Filed: Aug. 31, 2000

Related U.S. Application Data

(60) Provisional application No. 60/152,650, filed on Sep. 7, 1999.

(51) Int. Cl.$^7$ .................. A61K 39/00; A61K 45/00; A61K 39/395; A61M 37/00; G01N 33/53

(52) U.S. Cl. ................ 424/140.1; 424/233.1; 424/131.1; 424/159.1; 424/278.1; 424/93.1; 435/7.1; 530/351; 514/885; 604/4.01; 604/5.01; 604/5.02

(58) Field of Search .................. 435/7.1; 424/140.1, 424/233.1, 131.1, 159.1, 278.1, 93.1; 530/351; 514/885; 604/4.01, 5.01, 5.02

(56) References Cited

U.S. PATENT DOCUMENTS

| | | | |
|---|---|---|---|
| 4,328,183 A | 5/1982 | Rosenfield et al. |
| 4,375,414 A | 3/1983 | Strahilevitz |
| 4,813,924 A | 3/1989 | Strahilevitz |
| 4,880,751 A | 11/1989 | Georghegan |
| 5,707,812 A | 1/1998 | Horn et al. |
| 5,753,227 A | 5/1998 | Strahilevitz |
| 5,837,520 A | 11/1998 | Shabram et al. |
| 5,965,358 A | 10/1999 | Carrion et al. |
| 6,008,036 A | 12/1999 | Fanget et al. |
| 6,039,946 A | 3/2000 | Strahilevitz |

FOREIGN PATENT DOCUMENTS

| | | |
|---|---|---|
| WO | WO 97/17980 A1 * | 5/1997 |
| WO | WO 99/06562 A1 | 2/1999 |

OTHER PUBLICATIONS

Christ et al., Gene therapy with recombinant adenovirus vectors: evaluation of the host immune response, Immunology Letters, vol. 57, 1997, pp. 19–25.*

Gahery–Segard et al., Immune Response to Recombinant Capsid Proteins of Adenovirus in Humans, Journal of Virology, vol. 72, No. 3, 1998, pp. 2388–2397.*

"Therapeutic Apherisis In Russia: Is it Just Isolation or Original Development"; V. Aksenov; URL:"http://www.cpr.neva.ru/cpr/bomj/aksenov/therapeutic–apheresis.html" (6 pages), 2000.

Transplant Questions :Apheresis (1997) Indiana Blood and Bone Marrow Transplantation; URL:"http://www.ibmtindy.com/faq/apheresis.html" (2 pages).

D. Leff; "Cleansing Blood of Adenovirus Antibodies Lets Calydon's Virus Kill End–Stage Prostate Cancers"; Bio-World Today (vol. 11, No. 156, Aug. 14, 2000).

"Pre–Existent Adenovirus Antibody Inhibits Systemic Toxicity and Antitumor Activity of CN706 in the Nude Mouse LNCaP Xenograft Model: Implications and Proposals for Human Therapy"; Chen, et al. (2000) Human Gene Therapy 11:1553–1567.

(List continued on next page.)

*Primary Examiner*—Hankyel T. Park
*Assistant Examiner*—Stacy Brown
(74) *Attorney, Agent, or Firm*—Richard B. Murphy

(57) ABSTRACT

The present invention provides an apparatus and method to diminish the pre-existing immune response to the administration of a therapeutic virus by the selective elimination of antiviral antibodies from the serum. The present invention provides a chromatographic material for the elimination of such antibodies. The invention further provides plasmapheresis apparatus comprising this material. The invention further provides methods for the employment of such apparatus as part of therapeutic treatment regiments.

4 Claims, 9 Drawing Sheets

OTHER PUBLICATIONS

"Double filtration plasmapheresis in myasthenia gravis—analysis of clinical efficacy and prognostic parameters"; Yeh, J.–H. and Chiu, H.–C. (1999) Acta Neurologica Scandanavia 100:305–309.

"Purification of a Type 5 Recombinant Adenovirus Encoding Human p53 by Column Chromatography"; Huyghe, et al. (1995) Human Gene Therapy 6:1403–1416.

Platelet Sampling Protocol (2000) Gambro BCT, Inc. (10 pages).

Prosorba® Protein A Immunoadsorption Column: Essential Prescribing Information (1999) Cypress Bioscience, Inc. (URL:"http:www.cypressbio.com'package.html") (17 pages).

* cited by examiner

METHODS AND COMPOSITIONS FOR REDUCING IMMUNE RESPONSE

RELATION TO OTHER APPLICATIONS

The present application claims the benefit of U.S. Patent Provisional Application Serial No. 60/152,650 filed Sep. 7, 1999 pursuant to 35 U.S.C. §119(e).

BACKGROUND OF THE INVENTION

The therapeutic utility of wild type or recombinantly modified viruses are well known in the art. Early reports on the therapeutic use of viruses date from the 1950's. For example, in 1952, Southam and Moore reported on the use of Vaccinia, Newcastle Disease, West Nile, Ilheus and Bunyamwera, and Egypt 101 viruses for the treatment of a variety of cancers. Cancer 5:1025–1034 (1952). In 1956, Newman and Moore summarized the results of the treatment of fifty-seven cancer patients with a variety of viruses. Cancer 7:106–118. In 1956, Smith, et al. reported on the therapeutic use of adenovirus for the treatment of cervical cancer. Cancer 9: 1211–1218. Southam presented a summary of the clinical experience obtained at the Sloan-Kettering Institute on the efficacy of viruses as antineoplastic agents in 1960. Transactions of the New York Academy of Sciences 22:657–673. More recent reports demonstrate a continuing interest in the therapeutic use of viruses. Taylor, et al. presented results suggesting the therapeutic use of bovine enterovirus-1 for the treatment of solid and ascites tumors based on experiments conducted in mice. PNAS (USA) 68:836–840 (1971). Additional human clinical trials continued to demonstrate promise in this field as illustrated by the use of Mumps virus to treat a variety of cancers. Asada, T. (1974) Cancer 34:1907–1928.

An increased understanding the viral genome and the advent of recombinant DNA techniques permitted the manipulation of viruses to possess particular desirable features. For example, a recombinant adenovirus containing a modification to the E1B-55K region is currently in Phase II clinical trials in human beings. Additionally, recombinant viral vectors have been employed for the delivery of a variety of therapeutic substances. Most notably, recombinant adenoviral vectors have been employed in anti-cancer therapies where the viral genome has been modified to encode a tumor suppressor gene. In particular, a replication deficient virus expressing the p53 tumor suppressor gene has successfully completed Phase I and is currently in Phase II/III clinical development.

However, the clinical experience with such vectors has demonstrated that a significant fraction of the therapeutic virus which is administered to a patient is disabled by the presence of neutralizing antibodies in the serum and reticular endothelial system (RES). This obstacle is particularly acute when an adenovirus is used as the vehicle for delivery of a transgene since a act significant portion of the human population has naturally been exposed to adenoviruses vectors and possesses pre-existing immunity. Consequently, the administration of a significant excess of the recombinant adenoviral vector is administered to the patient to "dose through" the pre-existing immune response. Additionally, even if no pre-existing immune response was present, following administration of a therapeutic virus the mammal will generally produce an immune response to the virus. This "induced" antiviral immune response complicates additional courses of therapy with the therapeutic virus in a manner similar to the pre-existing immune response induced by exposure to the virus in the environment. This is not desirable from a clinical standpoint in that it may present complications to the already ill patient. Furthermore, from a commercial standpoint a large quantity of material is wasted in an attempt to dose through the preexisting immune response. Consequently, there is a need in the art to reduce the pre-existing immune response to therapeutic viral vectors.

A variety of methods have been employed in an attempt to cope with this problem. In one method, the virus is coated with masking agents such as polyethylene glycol (so called "PEGylation") to coat the virus and mask the immunological determinants of the virus. This is a cumbersome process requiring that the virus be coated with an agent and the long-term stability of the PEGylated virus has yet to be demonstrated as commercially feasible. Other avenues include co-administration of immunosuppressive agents. However, the administration of broad spectrum immunosuppressive agents is not desirable. In particular, there is mounting evidence to suggest that a significant complement to anti-cancer therapy is that the immune response augments the anti-tumor activity of the therapeutic virus. This phenomenon has been observed for some time and many individuals have suggested that amplification of the immune response to tumor antigens may be of therapeutic benefit. Consequently, it is not generally desirable to broadly suppress the immune system of a cancer patient.

Consequently there remains a need in the art to reduce the pre-existing humoral immune response to a therapeutic viral vector. The present invention addresses this need.

SUMMARY OF THE INVENTION

The present invention provides compositions, devices and methods to remove antiviral antibodies from the blood of mammals. The compositions and methods of the present invention may be practiced in conjunction with administration of a therapeutic virus. The invention further provides an immunoaffinity material comprising a chromatographic support material derivatized with antigenic determinants of viral coat. The invention further provides an improved apheresis apparatus to remove antiviral antibodies from the blood and, in particular from plasma. The present invention further provides therapeutic methods involving the use of such apparatus.

DETAILED DESCRIPTION OF THE INVENTION

The present invention provides a method for reducing the concentration of antiviral antibodies in a sample of plasma by contacting said isolated plasma with an immunoaffinity chromatographic material comprising an immunoaffinity material linked to a chromatographic support such that antibodies are retained on the immunoaffinity material.

The invention further provides a method of reducing the concentration of antiviral antibodies in a mammalian organism, said method comprising the steps of:
a) obtaining a sample of blood from said mammalian organism;
b) isolating the plasma from the cellular components from said blood sample;
c) contacting said isolated plasma with an immunoaffinity chromatographic material comprising an immunoaffinity material linked to a chromatographic support such that antibodies are retained on the immunoaffinity material;
d) reintroducing the cellular components isolated from step (b) and the purified plasma from step (c) to the mammal.

It will be readily understood by those skilled in the art that the procedures of step (d), i.e. the reintroduction of the cellular components and purified plasma, may occur simultaneously or be separated by some period of time. However, it is preferred that these procedures be performed contemperaneously.

The invention further provides an improved method of treating a mammal with a therapeutic virus wherein the improvement comprises reducing the concentration of antiviral antibodies in said mammal prior to the administration of said therapeutic virus by:

a) obtaining a sample of blood from said mammalian organism;

b) isolating the plasma from the cellular components from said blood sample;

c) contacting said isolated plasma with an immunoaffinity chromatographic material comprising an immunoaffinity material linked to a chromatographic support such that antibodies are retained on the immunoaffinity material;

d) reintroducing the cellular components isolated from step (b) and the purified plasma from step (c) to the mammal.

The invention further provides immunoaffinity chromatographic materials comprising components of the viral coat.

The invention further provides apparatus useful in the practice of the present invention.

The invention further provides an improvement to a method of treatment of a mammal with a therapeutic virus wherein the foregoing procedure is performed in advance of the administration of a therapeutic virus.

Antiviral Antibodies:

The term antiviral antibodies is used to describe antibodies which bind to viruses. These antibodies are generally produced by the mammalian humoral immune system by exposure of the mammal to a virus, either environmentally or therapeutically (e.g. vaccination or administration of a therapeutic virus). Antiviral antibodies comprise both neutralizing and non-neutralizing antibodies. The term neutralizing antibodies is used in its conventional sense to refer to antibodies which prevent the proliferation of infectious virus. When the method is used in conjunction with the administration of a therapeutic virus, removal of neutralizing antiviral antibodies is of greater concern than the removal of non-neutralizing antibodies as neutralizing antibodies are primarily responsible for inactivation of the therapeutic virus to be administered.

Blood:

The term "blood" is used in its conventional sense to refer to the blood of a mammal. A blood sample may be obtained from a living mammal by conventional blood collection procedures such as venipuncture or arterial puncture techniques. The lower risks and ease of access associated with venous collection procedures make venous blood the preferred source of blood for use in the present procedure. Venous blood may be collected by syringe or evacuated collection vessels such as the Vacutainer® brand blood collection system (commercially available from Becton-Dickinson Corporation, Franklin Lakes, N.J.) for batchwise treatment according to the method of the present invention. However, the quantities of blood generally treated to provide dimunition of antiviral antibody response in a living mammal, in the preferred practice of the invention the blood is collected in a continuous process for introduction to a plasmapheresis apparatus by venous catheter. The proximal end of a catheter is inserted into the vein of the mammal using conventional venipuncture techniques and the distal end of the catheter is connected to the inlet port of a plasmapheresis apparatus. A plasmapheresis apparatus generally comprises a pump mechanism to drive the isolated blood through a means for isolating plasma from cellular blood components, wherein the cell rich blood is returned to the mammal while the plasma is directed for storage or further processing.

The range of mammals subject to therapeutic virus therapy are varied and certain sources are preferred for the isolation of venous blood. In cattle or sheep, jugular catheterization is preferred. In rabbits, the median ear artery, ear vein, or carotid artery are preferred. In pigs, the ear vein is preferred. In non-human primates, the saphenous, cephalic, and femoral veins are preferred sources of venous blood. In cats, the cephalic, femoral, jugular and saphenous veins are preferred. In dogs, the cephalic, jugular, and saphenous veins are preferred. In human beings, the cephalic and saphenous veins are preferred sources of venous blood, cephalic being most preferred.

Isolation of Plasma: Plasmapheresis

Blood is a complex mixture of cellular and solubilized fluid components. The fluid portion of blood (plasma) comprises a variety of dissolved nutrients, waste products and solubilized proteins such as antibodies. The term "plasmapheresis" refers to an apheresis procedure in whereby blood removed from a mammal is separated into plasma and cellular blood components, the plasma being isolated for further processing. The principles and practice of apheresis are well known in the art. Standard procedures for apheresis are described in *Apheresis: Principles and Practice* commercially available from the American Association of Blood Banks, 8101 Glenbrook Road, Bethesda, Md. 20814-2749 as Stock #PC98-972003.

Plasmapheresis is currently performed in clinical arena using continuous flow centrifugal separators, which separate cells by density; flat-sheet and intra-lumenal hollow fiber membrane devices, which operate by tangential flow microfiltration; and rotating membrane devices, which enhance microfiltration flux by inducing Taylor vortices. Such devices are commercially available and are well known in the literature, see, e.g. Plasmapheresis: Therapeutic Applications and New Techniques, Nose Y, et al., Raven Press, New York (1983); Kessler S. B., Blood Purif., 11:150–157 (1993);. See, also Fischel, U.S. Pat. No. 5,783,085 issued Jul. 21, 1998; Kessler, et al., U.S. Pat. No. 5,846,427 issued Dec. 8, 1998; Ash, U.S. Pat. No. 5,919,369 issued Jul. 6, 1999, Ball, et al. U.S. Pat. No. 5,914,042 issued Jun. 22, 1999; Fischel, U.S. Pat. No. 5,464,534 issued Nov. 7, 1995; Bensinger, U.S. Pat. No. 4,614,513 issued Sep. 30, 1986; Terman, et al. U.S. Pat. No. 4,215,688 issued Aug. 5, 1980;

and Pollard, Jr., U.S. Pat. No. 4,464,165 issued Aug. 7, 1984, the teachings of which are herein incorporated by reference.

Figure 6:
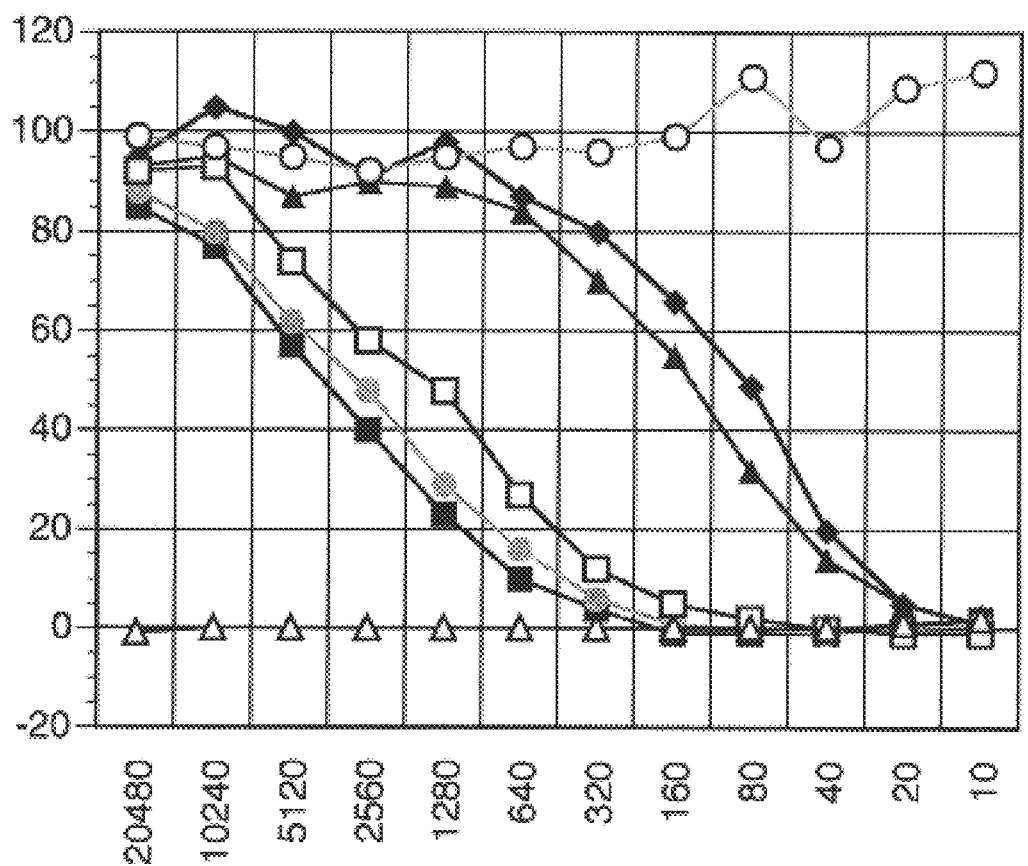
FIG. 6 is a graphical representation of the results of experiments conducted to compare the efficiency of different columns in removing adenoviral neutralizing antibodies obtained from the exposure of pooled human sera exhibiting a high neutralizing anti-adenoviral titer (ID50>1280). The vertical axis is percent transduction which is inversely correlated with percentage of neutralizing capacity. The horizontal axis represents neutralizing antisera titer. The filled squares represent primed serum; the shaded circles represent serum depleted over a Prosorba® protein A column; the diamonds represent serum depleted over an adenoviral capsid SAVID column; the filled triangles represent bound antibodies eluted from a Prosorba® column; the open circles represent hela cells transduced with a recombinant adenovirus encoding the green fluorescent protein (rAd-GFP) in the absence of antisera; the open squares represent antibodies eluted from a capsid SAVID column; and the open triangles represent HeLa cells as a background control (no virus, no antibodies).
Figure 7:
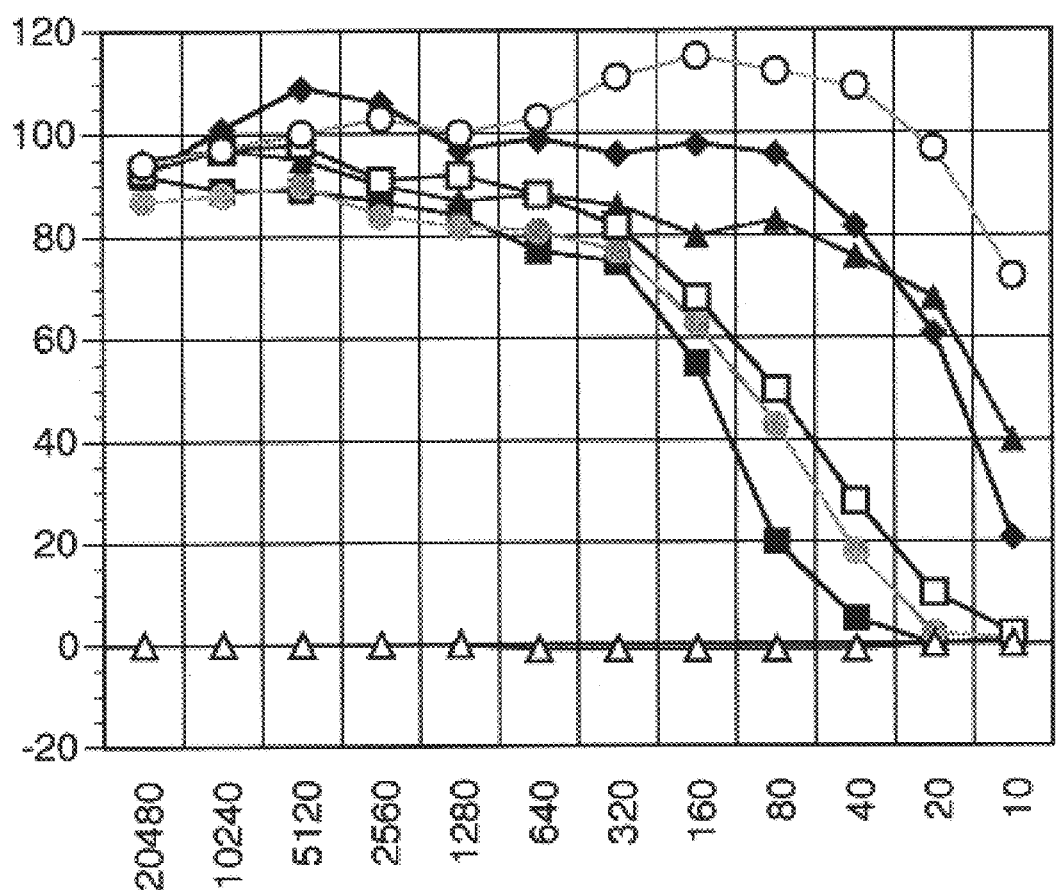
FIG. 7 is a graphical representation of the results of experiments conducted to compare the efficiency of different columns in removing adenoviral neutralizing antibodies obtained from the exposure of pooled human sera exhibiting a low neutralizing anti-adenoviral titer (ID50<320). The vertical axis is percent transduction which is inversely correlated with percentage of neutralizing capacity. The horizontal axis represents neutralizing antisera titer. The shaded squares represent primed serum; the shaded circles represent serum depleted over a Prosorba®protein A column; the shaded diamonds represent serum depleted over an adenoviral capsid SAVID column; the shaded triangles represent bound antibodies eluted from a Prosorba® column; the open circles represent HeLa cells transduced with rAd-GFP in the absence of antisera; the open squares represent bound antibodies eluted from the SAVID adenoviral capsid column; and the open triangles represent HeLa cells as a background control (no rAd-GFP virus, no antibodies).
Figure 8:
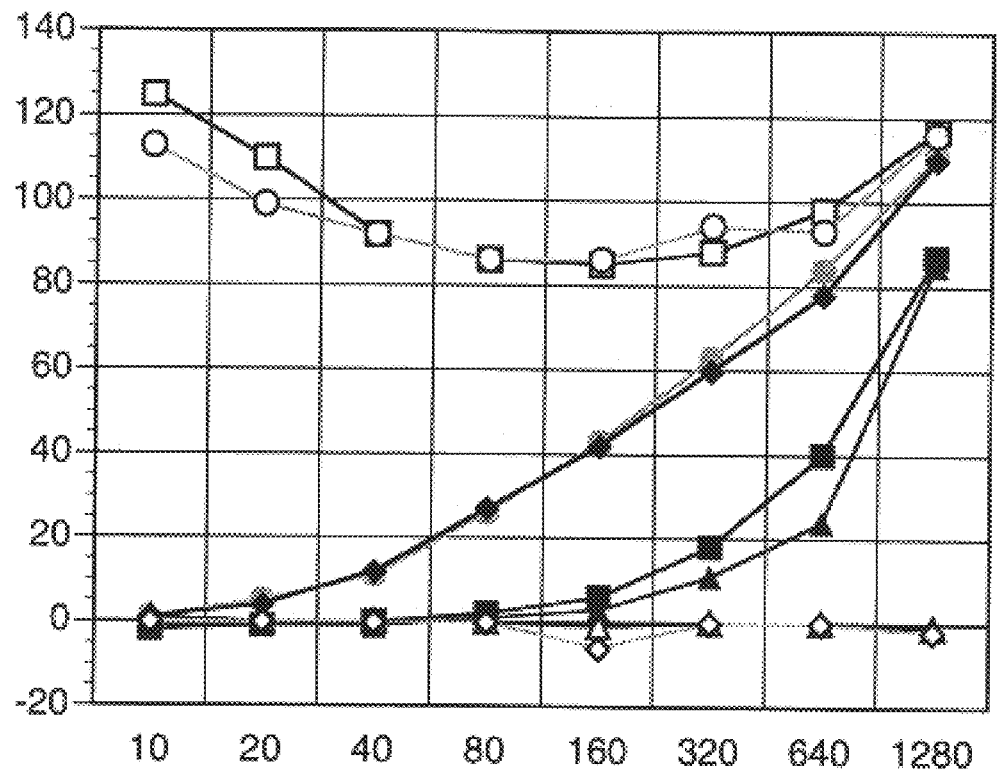
FIG. 8 is a graphical representation of the results of experiments conducted to compare the efficiency of a protein G column relative to a capsid SAVID column in removing adenoviral neutralizing antibodies obtained from the exposure of pooled human sera exhibiting a high neutralizing anti-adenoviral titer (ID50>1280) or low neutralizing antibody titre (ID50<320). The vertical axis is percent transduction. The horizontal axis represents neutralizing titer. The shaded squares represent antibodies eluted from an adenoviral capsid SAVID column using high titer antiserum; the shaded circles represent antibodies eluted from an adenoviral capsid SAVID column using low titer antiserum; the shaded triangles represent antibodies eluted from a protein G column using high titer serum; the shaded diamonds represent antibodies eluted from a protein G column using low titer serum; the open circles represent HeLa cells transduced with a rAd-GFP in the absence of antisera; the open squares represent HeLa cells transduced with rAd-GFP in presence of antisera and the open triangles represent HeLa background control with normal serum; and the open diamonds represent HeLa background control without serum.

Immunoadsorbent/Immunoaffinity Material:

The terms "immunoaffinity material" or "immunoadsorbent material" are used interchangeably herein to refer to material which binds to antibodies. A variety of immunoadsorbent materials are well known in the art such as *Staphyloccus aureus* protein A, recombinant protein A and G, KappaLock™ (Zymed). The use of generalized immunoadsorbent material (such as protein A) or protein G results in general elimination of circulating antibodies and is not necessarily specific with relation to the potentially antigenic therapeutic virus to be administered. Protein A binds preferably to IgG class antibodies (and to some extent to IgA and IgM antibodies) and is not selective for any particular antibody type. Although these general immunoadsorbent materials are not necessarily specific to a particular type of antibody, they are nonetheless useful immunoadsorbent materials which may be employed in the practice of the present invention as shown in the data presented in FIGS. 6, 7, and 8 of the attached drawings.

In the preferred practice of the invention the immunoadsorbent material is prepared with respect to the particular therapeutic virus to be employed in order to achieve selective elimination of antiviral antibodies specific to that virus by the linkage of a viral epitope or epitopes to the chromatographic support. As previously discussed, the broad elimination of serum antibodies has the potential to eliminate any circulating anti-tumor antibodies which are a potentially important adjunct to successful chemotherapy and potentially leaves one more susceptible to opportunistic infections. Consequently, selective removal of antibodies to the particular therapeutic virus being employed is preferred. In particular, the present invention provides a selective antiviral immuno-depletion ("SAVID") chromatographic material comprising a viral epitope conjugated to a chromatographic support. The acronym SAVID is employed as shorthand for selective antiviral immuno-depletion. Selective, emphasizing the nature of the process whereby the antibodies against the therapeutic virus to be used are selectively eliminated from the plasma. Antiviral, emphasizing that the methods and devices are designed to eliminate the pre-existing or induced immune response to therapeutic viruses. Immuno-Depletion, emphasizes the feature of the invention in that the immune response, particularly the level of plasma antiviral antibodies, is transiently reduced. Through the use of a viral epitope as the immunoadsorbent material, selective reduction of antiviral antibodies from the plasma is achieved, the antiviral antibodies present in the bloodstream being retained on the SAVID chromatographic material. As a result of this process, the pre-existing or induced humoral immune response to a specific type(s) of therapeutic viral vector(s) is selectively diminished resulting in increased transduction efficiency from a given dosage of the viral vector. Concomitantly, this permits a lower viral dosage to achieve an equivalent therapeutic response in the absence of this procedure.

The term "epitope" is used herein in its conventional sense to refer to the structure on an antigen that interacts with the combining site of an antibody or T-cell receptor as a result of molecular complementarity. The term "viral epitope" is used to refer to epitopes of viral surface proteins. Epitopes may be naturally occurring or synthetic mimetics. The epitope employed may represent the entire viral coat protein or antigenic determinant fraction thereof. For example, in order to present the viral epitope, a viral coat protein may be conjugated to the column. Alternatively, a fragment of the viral coat protein may be employed which retains the primary antibody binding site. The epitope may also be a synthetic peptide or protein and is used to collectively refer to naturally occurring or synthetic peptides which comprise the antigenic determinants of viral surface proteins. The determination of those regions of a protein most responsible for antibody binding can be determined by procedures known in the art. For example, the DIRECT™ methodology, instrumentation and procedures commercialized by Argonex, Inc., 2044 India Road, Charlottesville Va. 22901 provides a means to identify the individual peptides that stimulate a CTL response. These peptides may be modeled using conventional molecular modeling software to generate non-peptidyl small molecule epitope mimetics. These individual peptides or small molecule mimetics representing a particular epitope of a protein may be conjugated to the chromatographic support in lieu of using the entire viral surface protein.

In the preferred embodiment as exemplified herein, the viral surface antigenic moieties comprise the viral coat proteins of the adenovirus. These may be readily obtained as by-products of the production of recombinant virus or be produced by recombinant DNA techniques for the production of proteins well known to those of skill in the art. Methods for the high titer production of viruses are provided in Giroux, et al., U.S. Pat. No. 5,994,134 issued Nov. 30, 1999 the entire teaching of which is herein incorporated by reference. For example, a recombinant adenovirus preparation was subjected to column chromatography as described in Shabram, et al. (U.S. Pat. No. 5,837,520 issued Nov. 17, 1998 the entire teaching of which is hereby incorporated by reference). The chromatography eluent provides the purified adenovirus with a variety of contaminants comprising viral coat proteins such as penton, hexon, 3A, fiber proteins of the adenovirus. These additional "contaminants" representing useful epitopes may be purified to homogeneity from the column eluent by conventional chromatographic procedures. The identities of these proteins may be easily confirmed by the use of commercially available antibodies specific against the adenoviral capsid. Such antibodies are commercially available from a variety of sources Chemicon and Lee BioMolecular. Alternatively, monoclonal antibodies to such proteins may be generated by techniques well known to those of skill in the art.

Linked:

The term "linked" is used herein to describe a kinetically stable association with and is used interchangeably with the terms conjugated or cross-linked. A stable interaction between the immunoadsorbent material and the chromatographic support may be achieved be by ionic, affinity, covalent cross-linking, kinetically labile coordinate covalent cross-linkages (Smith, et al. U.S. Pat. No. 4,569,794), or kinetically inert coordinate covalent cross-linkages as described in Anderson, et al. (U.S. Pat. No. 5,439,829 issued Aug. 8, 1995). In one embodiment of the invention as exemplified herein, the viral epitopes are adsorbed onto the surface of an affinity gel (Affi-Gel®). The Affi-Gel® product is available in two different versions: Affi-Gel® 10 (BioRad Catalog No. 153-6046) and Affi-Gel® 15 (BioRad Catalog No. #153-6052). The proper use of either product (or a mix of the two) is determined by the pI of the epitope to be coupled. The Affi-Gel column couples free alkyl or amino groups. A commonly employed buffer, Tris, will couple to the column effectively. Consequently, it is important when using such columns to avoid the use of Tris buffers. Alternative to the use of Tris, cell lysis, wash, column loading/ washing and elution is all performed using buffers made with MOPS or HEPES rather than Tris. Detailed instructions on performing the coupling of the protein in 0.1 M MOPS to the matrix are available from the manufacturer. Approximately 0.5 ml (packed volume) of matrix binds approximately 20 mg of protein. Coupling is achieved by mixing and allowing the reaction to proceed for approximately 4 hours at 4° C. The efficiency of coupling is determined by comparing the free protein concentration before and after the coupling reaction. Following coupling reaction, it is preferred to block any unreacted esters. This can be readily achieved by removing the excess protein and adding 1M ethanolamine pH8.0, with mixing at 4° C. for an hour. Excess ethanolamine is rinsed from the column with TBS. The column may be stored for extended periods at 4° C. in TBS plus 0.2% sodium azide.

Alternative to linking through the free amino groups, one may also link the epitope to the column matrix via free cysteine residues. For example, a cysteine residue can provide a stable thio-ether bond to Epoxy-Sepharose®-6B (commercially available from Pharmacia). This may be employed to link the C-terminus of the epitope by the addition of a C-terminal cysteine residue. The coupling reaction may be achieved by addition of the epitope to 1.0 ml of pre-swollen Epoxy-Sepharose-6 B® in 0.1M $NaHCO_3$ pH9.0 in a small reaction volume with constant mixing at 37° C. for 24 hours. Washing with 50 ml of 0.1M $NaHCO_3$ pH9.0, then block unreacted groups on the matrix by incubating the 1.0 ml of resin in 5.0 ml of 0.1M 2-mercaptoethanol with gentle agitation.

Chromatograihic Support:

The term "chromatographic support" is used in its commonly accepted definition as the basic element of an affinity chromatography matrix. The principles of immunoaffinity chromatography are well known in the art. See, e.g. Mohr, et al. (1992) Immunosgmtion *Techniques: Fundamentals and Applications*, ISBN#3055013506. Common chromatographic supports include natural or synthetic polymers in the form of a membrane, bead (microparticle), resins, or tube. Common materials include agarose (a polymer of D-galactose and 3,6-anhydro-L-galactose), polystyrene, polyethylene, etc. and are well known to those of skill in the art. In the preferred practice of the invention, the chromatographic support is a cross-linked activated agarose gel such as the Affi-Gel® 10 or Affi-Gel® 15 supports commercially available from Bio-Rad.

Contacting:

The isolated serum is may be brought into contact with the with the immunoaffinity chromatographic material in a variety of contexts. The immunoaffinity chromatographic material may be used in batch preparations whereby the blood is exposed to a quantity of the material, but generally will be formed into a column for use with a conventional plasmapheresis apparatus. The column may either be a packed bed column comprising a stationary phase in a granular form and packed so as to form a homogenous bed wherein the stationary phase completely fills the column. Alternatively, open tubular columns may be employed wherein the stationary phase comprising the viral epitope is deposited as a thin film or layer on the column wall and possessing a central passage to permit passage of the mobile phase. In such instances, a plurality of small diameter tubular materials are employed to maximize the exposure of the viral epitopes to the mobile phase.

Alternatively the immunoaffinity chromatographic material may be in liquid form but possessing a greater or lesser density than blood products such that the blood products can be exposed to the chromatographic material and easily separated. For example, capsid proteins could be bound to a dense material conjugated to a liquid polymer whose density would be, for example, 1.35. The materials could be mixed in batch mode with the isolated blood product. The blood components binding to the material could then be separated by centrifugation. Alternatively, the immunoaffinity chromatographic material capable of phase separation could be mixed with the blood and separated in a centrifugal partition chromatography device. Centrifugal countercurrent chromatographic devices and procedures are known in the art. Either the immunoaffinity chromatographic material or the blood or plasma could be employed as the mobile phase in such procedures.

The antibodies retained on immunoaffinity chromatographic support may be removed to regenerate the column for repeated use. However, the immunoaffinity chromatographic material is preferably made from disposable materials and is disposed of following use to ensure that the materials isolated from one patient and retained on the column by ineffective washing procedures are not leeched from the column and introduced into the bloodstream of a second patient.

Figure 9:
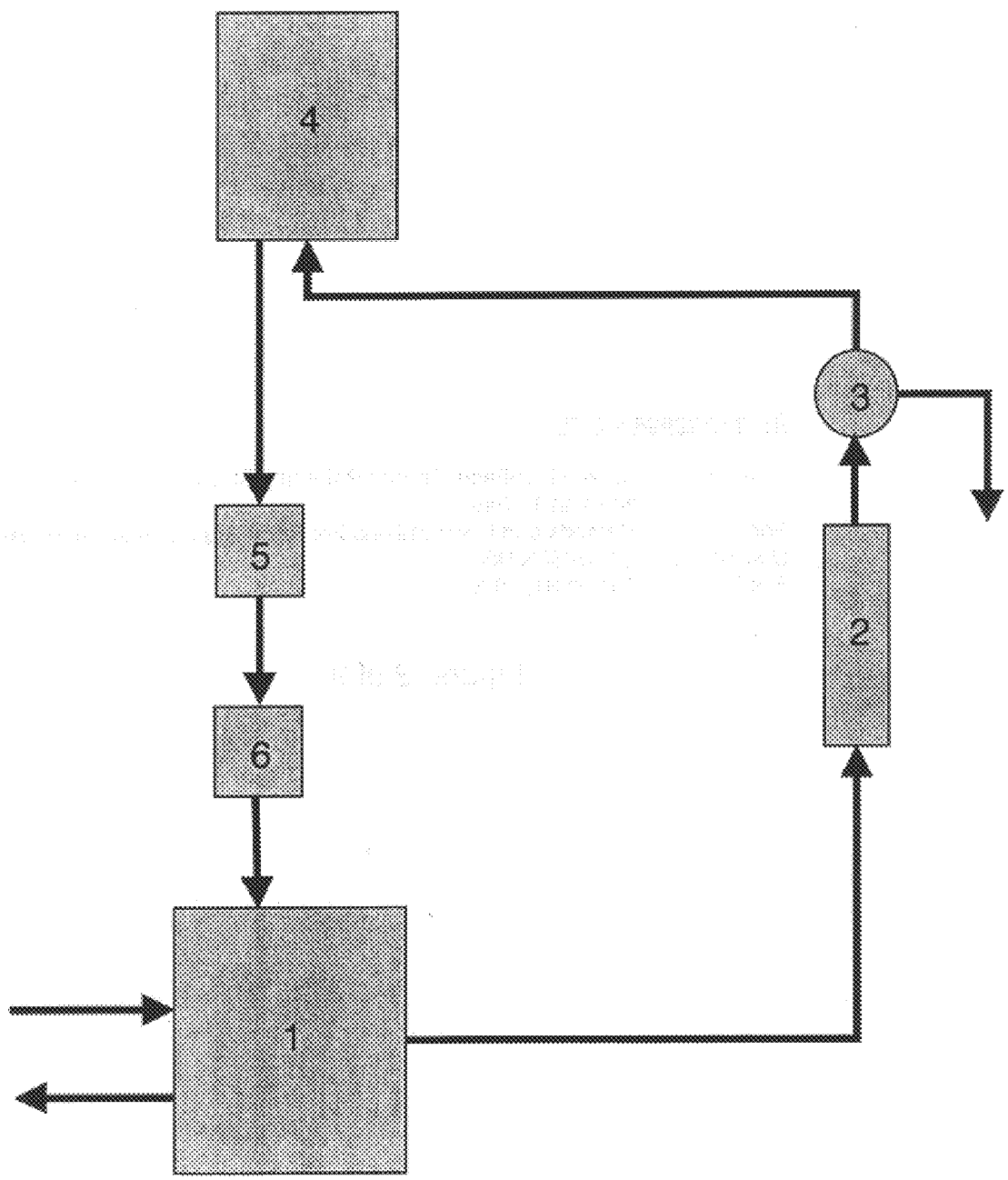
FIG. 9 is a schematic representation of one orientation of the apparatus used in the practice of the present invention. The arrows represent the direction of the flow of blood materials through the apparatus. Item 1 represents a plasmaphersis apparatus. Item 2 represents an immunoaffinity chromatographic material in column format. Item 3 represents a 3-way valve. Item 4 represents a storage vessel for purified plasma. Item 5 represents a filter apparatus to remove microaggregates from the purified plasma prior to reintroduction. Item 6 represents a drip chamber.

It will be readily apparent to those of skill in the art that the plasma produced following passage over the immunoadsorbent material may be stored for later use. However, in the preferred practice of the invention, the purified plasma is reintroduced into the circulation system of the subject contemporaneously with the purification process. The term "contemporaneously" generally means less than about three hours, preferably less than one hour. In the most preferred practice of the invention to avoid the complications associated with losses in blood volume in live mammals, the foregoing process is run in a continuous mode using an apparatus such as the apparatus schematically represented in FIG. 9 of the attached drawings.

In order to demonstrate that the present method is useful in the reduction of serum neutralizing antiviral antibodies, serum of mice exposed to human adenovirus was subjected to purification on a Protein A column and a KappaLock™ sepharose column (commercially available from Zymed Laboratories, Inc., South San Francisco, Calif. as catalog No. 10-1841) which retains primarily IgG, IgM, and IGA class immunoglobulins and assayed for neutralizing anti-Ad antibodies. In particular, the blood of mice possessing pre-existing anti-adenoviral antibodies was isolated, the serum separated and exposed to a Protein A chromatographic resin. The levels of serum neutralizing anti-adenoviral antibodies before and after the procedure was determined in substantial accordance with the teaching of Example 3 herein. Moreover., neutralizing antibody could be effectively depleted in-vitro with a column consisting of rAd proteins linked to a bead rAd affinity column). In this experiment, serum purified on a Protein A column or KappaLock™-Sepharose column showed a reduction in serum neutralizing antibody titer.

Figure 3:
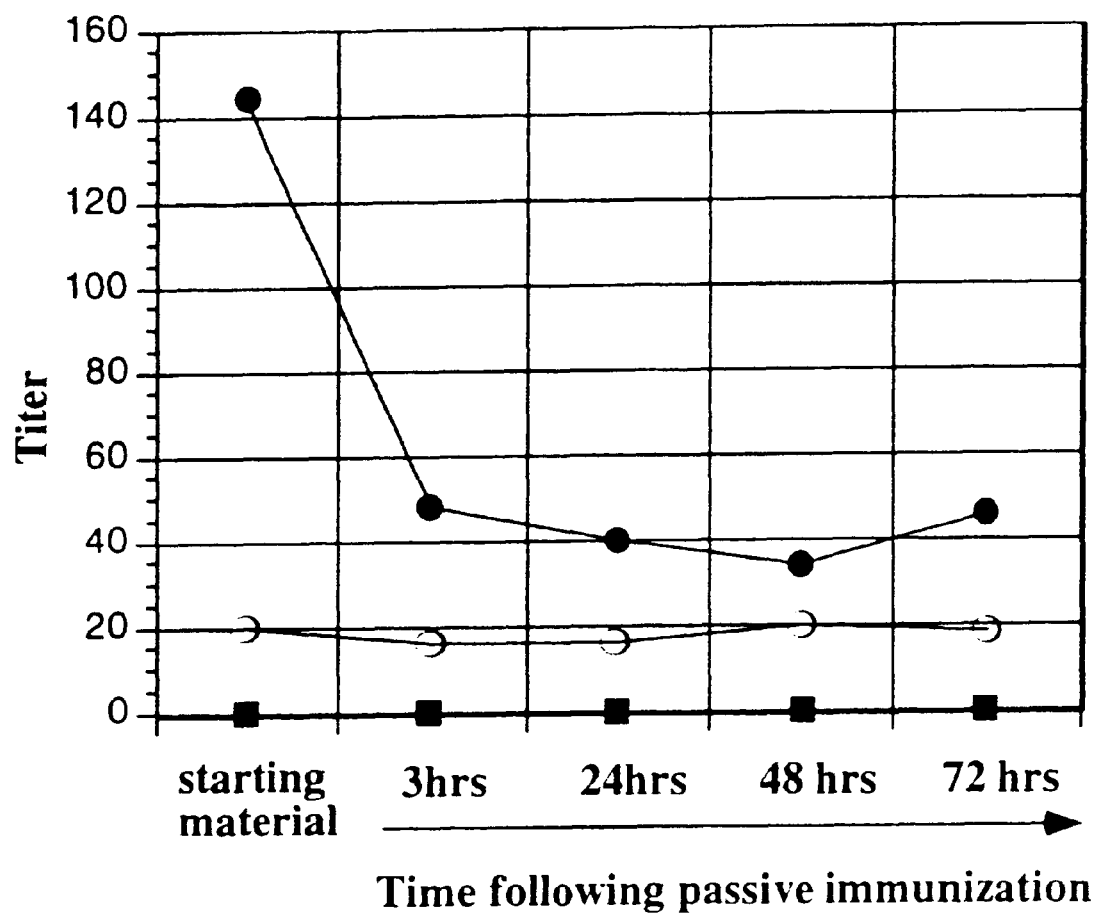
FIG. 3 is a line graph showing that the passive immunization procedure does result in serum neutralizing antibodies in the recipient host animal. The vertical axis represents antibody titer. The horizontal axis represents time (hours) following passive immunization. As can be seen from the data presented, the presence of serum neutralizing antibodies is observed within three hours of passive immunization and remains stable over a period of at least 72 hours. Note that the injected material (0.5 ml) is essentially diluted to the normal blood volume of the mouse and then remains stable for at least 72 hours.

The utility of a SAVID immunoadsorbent material was further demonstrated in an in vivo mouse passive immunization model. Since conventional plasmapheresis procedures are not feasible in mice and mice do not innately possess anti-human adenoviral antibodies, "passive immunization" procedure was used to create a model system to mimic plasmapheretic removal of anti-adenoviral antibodies. Passive immunization refers to a procedure whereby the serum of one animal is introduced into a second animal. In this instance, a group of BALB/c mice were injected with recombinant human adenovirus (hAd) in order to develop anti-hAd antibodies. These mice were sacrificed and the sera were collected. This serum was then injected intraperitoneally into a second group of synergenic BALB/c mice. In order to ensure that this passive immunization procedure was effective at transmitting the ant-hAd antibodies to the serum of the intraperitoneally injected mice in the second group, a pilot study was conducted to show that 10 µg of anti-adenoviral antibody eluted from the rAd -column, or equivalent amount of serum (in a total volume of 500 µl) injected intraperitoneally can be detected in the serum of naive BALB/C mice. The results of these experiments are presented in FIG. 3 of the attached drawings. As can be seen from the data presented, anti-hAd antibodies were present in the serum as soon as 3 hours post IP administration and were still detectable 72 hours after IP injection. The serum (500 µl) was diluted by the normal serum volume in the mouse and then remained stable for at least 72 hours. These results indicate that mice injected intraperitoneally with serum containing anti-adenoviral antibodies effectively transfer humoral immunity (i.e. neutralizing antibodies to adenovirus) and provides a valid model system for demonstrating the effectiveness of the present invention.

A recombinant adenovirus (ZZCB) was used to prime the mice with a recombinant human adenovirus to generate a "pre-existing" immune response for later evaluation. The method of preparation of the ZZCB and BGCG vector is described in Gregory, et al., supra, and are referred to in that reference as the A/C and A/C/β-gal viruses respectively. BALB/c mice were injected with $5 \times 10^{10}$ particles of ZZCB. The mice were then given a booster injection of $5 \times 10^{10}$ particles 28 days following the first injection. The mice were sacrificed 14 days following the second injection and the serum isolated and pooled. A cross-linked agarose column was prepared in substantial accordance with the teaching of Example 1 herein using multiple human adenoviral capsid proteins cross-linked to the column as a source of epitopes. One fraction of the pooled serum was allowed to equilibrate with the column material and eluted (referred to hereinafter as "purified serum") and the remaining fraction of the pooled serum was retained as a control (hereinafter referred to as "unpurified serum").

Figure 4:
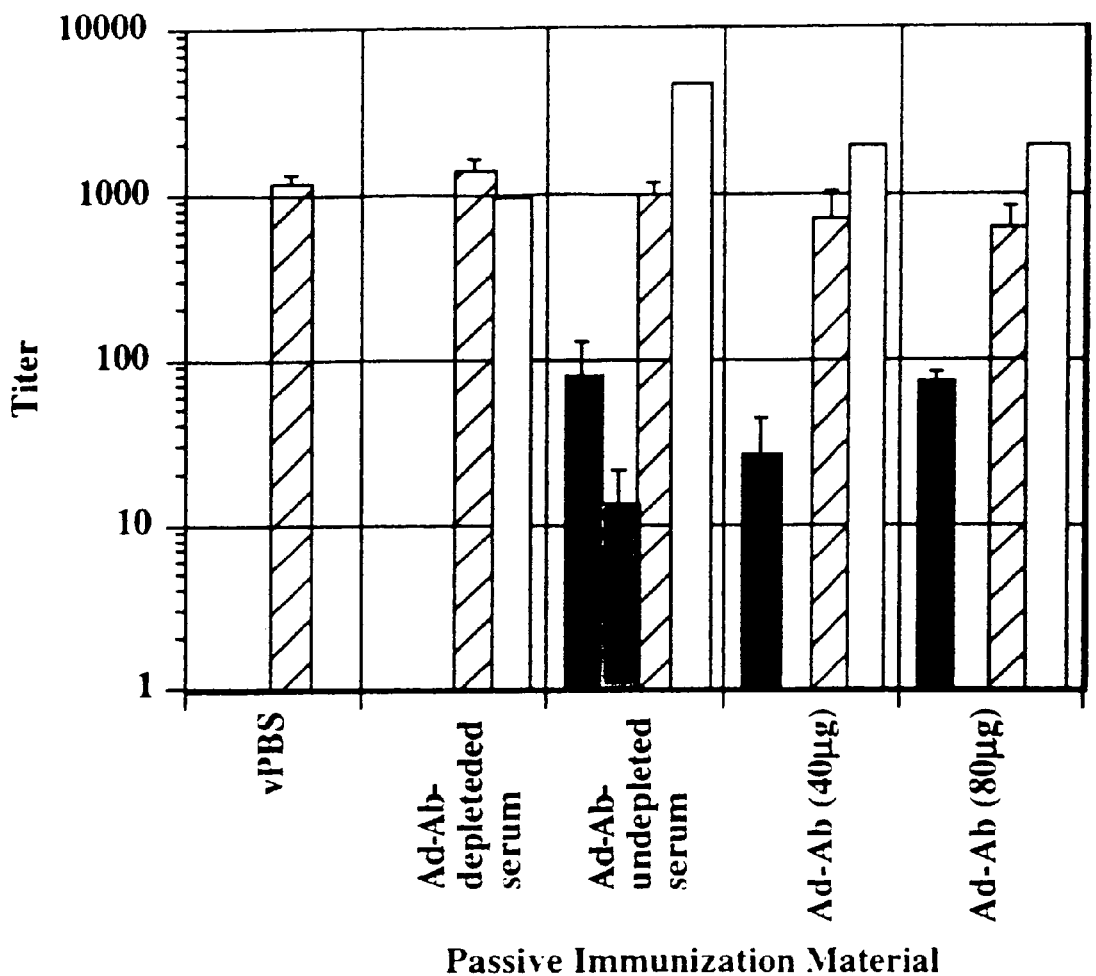
FIG. 4, is a graphical representation of serum neutralizing antibody capacity (ID-50) following passive immunization and subsequent dosing with an adenovirus expressing β-galactosidase (BGCG). The vertical axis represents antibody titer and the horizontal axis represents time in hours following administration of virus. Each panel represents the material which was used for passive immunization (i.e. vPBS control, Ad-Antibody undepleted serum, Ad-Ab depleted serum: Ad-Ab). The black bars show titer of neutralizing one hour following passive immunization. The gray bars show neutralizing antibody titer two hours following virus dosing after passive immunization. The hatched columns show neutralizing antibody titer three days following virus dosing after passive immunization. The white bars reflect neutralizing antibody titer of the materials used for passive immunization. The data show that an antibody response by the host is mounted within 3 days. Moreover, the data show that the injection of rAd by intravenous route further depletes neutralizing antibodies from the sera within 2 hours. The data also suggest that almost all the high affinity antibody in the major coat proteins are depleted following injection of rAd by intravenous route, eluted from the column. (see the data relating to Ad-antibody at 40 µl).

Five mice were each injected intraperitoneally with 40 µg of anti-hAd antibodies eluted from the rAD-protein column, 80 µg of anti-hAd antibodies eluted from rAd-protein column, column-depleted serum, untreated serum from primed animals and serum from vPBS (phosphate buffered saline further containing 2 mM $MgCl_2$, 3% sucrose) injected animals and a sample of blood obtained one hour following passive immunization (to use as a standard) and allowed to rest overnight. The following day (approximately 12 hours post passive immunization), the mice were injected via the tail vein with $5 \times 10^{10}$ particles of the BGCG recombinant human adenovirus. Serum was collected at 2 hours post injection and the serum was analyzed for the presence of serum neutralizing anti-adenoviral antibodies. The mice were sacrificed at 3 days following injection of BGCG and the serum analyzed for the presence of serum neutralizing anti-adenoviral antibodies and liver tissue was analyzed for B-gal expression. The results of these experiments can be seen in FIG. 4 of the attached drawings. Animals receiving passive immunization with unpurified serum or 40 µg or 80 µg of anti-hAd antibodies eluted from the column demonstrated a high titer of serum neutralizing anti-hAd antibodies one hour following IP injection. However, those animals which were passively immunized with column-depleted serum, had a no detectable serum neutralizing antibodies at one hour post injection. The presence of neutralizing antibodies in all five groups of mice on the third day following BGCG injection is due to a primary humoral response to BGCG by the. Consequently, the level of serum anti-hAd neutralizing antibodies in those animals passively immunized with purified serum was substantially diminished relative to those animals receiving unpurified serum indicating that removal of antiviral antibodies is useful in vivo to minimize the pre-existing immune response to such viruses. The serum purified over a SAVID column showed a improved reduction in serum neutralizing anti-hAd antibodies relative to the Protein A and KappaLock™-Sepharose columns in vivo. Also evident from the data in FIG. 4 was that the intravenous injection of BGCG resulted in a further decrease in neutralizing antibodies in the sera (see undepleted serum two hour post virus). Moreover, in the group that received rAd antibody eluted from columns, virtually all the neutralizing antibody was depleted from the serum following injection of the BGCG by intravenous route. Thus systemic administration of rAd depletes serum neutralizing antibody and suggests that high affinity antibodies are depleted very efficiently. Thus readministration one hour or one day after injection of rAd may further promote redosing.

Perhaps more important to the clinician and from a commercial standpoint is the fact that the diminution of the pre-existing or induced humoral immune response permits the use of a lower dose of virus to achieve the same level of therapeutic transgene expression. This was demonstrated by examining β-galactosidase expression in the livers using the animals from the previous experiment. It is known from previous experiments that the majority of expression of systemically administered replication deficient adenovirus results in transduction of the cells of the liver. Consequently, upon sacrifice of the animals from the previous experiment, the livers were removed and assayed for β-galactosidase activity as an indicator of BGCG transduction efficiency. The results are presented in the photo micrographs in FIG. 5 of the attached drawings. These data provide evidence of the relative levels of β-galactosidase expression in livers from animals receiving passive immunization of column-depleted serum, undepleted serum, anti-hAd antibodies eluted from the rAd protein column serum from animals tests with vPBS. The data demonstrate that the level of expression of 0-galactosidase expression in mice receiving column depleted the serum is substantially greater than those mice receiving undepleted sera. Challenging these passively immunized mice with a dose of virus showed that transduction of virus was not detectable in livers of mice passively immunized with Ad-unadsorbed serum, however virus transduction was readily detected in livers of mice passively immunized with Ad-preadsorbed serum. Consequently, these experimental results demonstrate that the present invention is useful in vivo to increase transduction efficiency from recombinant adenoviral vectors in mammalian systems possessing pre-existing serum neutralizing antibodies. In particular, these data demonstrate that effective immunodepletion of anti-adenoviral antibodies can reduce the dosage of virus administration for transduction to achieve equivalent levels of transgene expression in the target tissues.

In order to determine the effects of this procedure in the human population, a series of experiments were conducted using human blood containing anti-adenoviral antibodies. Human serum from normal donors was obtained from the San Diego Blood Bank. The neutralizing capacity of each sample was determined by the GFP assay described in Example 3 herein. The serum was characterized as having high or low neutralizing capacity. Low neutralizing capacity was defined as a titer of 1:320 or less. High neutralizing capacity was defined as a titer of 1:2500 or more. The serum samples exhibiting either "high" or "low" neutralizing capacity were pooled and subjected to column chromatography over a Protein G column (commercially available from Zymed) and SAVID adenoviral capsid column (prepared in substantial accordance with the teaching of Example 2 herein). The results are presented in FIGS. 6, 7, and 8 of the attached drawings. The results demonstrate a significant reduction in serum neutralizing capacity following passage over the SAVID column. Furthermore, the results demonstrate that the antibodies eluted from the protein G column exhibited the same titer as the antibody eliminated form the capsid column suggesting that the efficiency of the protein G column and capsid column was similar in removing antiadenoviral antibodies.

It will be readily apparent to the skilled artisan that a combination of the above immunoadsorbent materials may also be employed. Such materials may be used together in a heterogenous mixture or sequentially to achieve improved reduction in antibodies from the serum or to remove antibodies of various types in a single plasmapheresis procedure.

Apparatus:

The present invention further provides a plasmapheresis apparatus wherein the plasma filtration element of such apparatus comprises an immunoaffinity chromatographic material comprising a viral epitope conjugated a chromatographic support. The plasma filtration elements of such devices is modified to incorporate an immunoaffinity chromatographic material in column format which is used to eliminate antiviral antibodies from blood plasma. Such apparatus is provided in schematic form in FIG. 9 of the attached drawings.

The immunaodsorbent material linked to the chromatographic support is generally to be supplied in kit of parts comprising the immunoadsorbent material linked to the chromatographic support packaged with instructions for the proper use of the material. In the preferred embodiment, the immunoadsorbent material linked to the chromatographic support is contained in an aseptic vessel constructed capable of sterilization such as glass or plastic (e.g. polycarbonate plastic). Preferably, the vessel is substantially cylindrical in shape defining a top and bottom surface, each of which top and bottom are provided with a centrally located nipple for attachment to the flexible tubing conventionally used in apheresis procedures to permit passage of the plasma through the vessel. The vessel optionally comprises a membrane element of pore diameter sufficient to permit the free flow of plasma but insufficient to allow passage of the immunoadsorbent material. The vessel containing the immunoadsorbent chromatographic material is generally to be provided in sterile packaging materials facilitating its sterility immediately prior to use. The kit of parts may optionally comprise a means for attaching the vessel to a support means and to maintain the vessel in a substantially vertical position during its use. Examples of such attachment means are well known in the art such as the Catalog No. 05-769 adjustable 3-prong clamp commercially available from Fisher Scientific. The kit of parts may optionally include flexible sterile tubing facilitating connection to conventional apheresis apparatus. The kit of parts may optionally include sterile heparinized luer lock 3-way valves to facilitate the draining of unwanted material from the essentially closed loop apparatus. The kit of parts may optionally include a leukocyte filter (e.g. Pall PL100® filter commercially available from Pall Corporation, 2200 Northern Boulevard, East Hills, N.Y. 11548) to facilitate the removal of microaggregates. The kit of parts may optionally include a drip chamber to avoid the introduction of air to the line returning to the patient's venous supply.

Applications:

As previously described, the method and apparatus of the present invention may be used in combination with the administration of therapeutic viruses to a mammal wherein the process for removing antiviral antibodies from the subject is performed in advance of the administration of a therapeutic virus. It should be noted that the present invention may be used to remove pre-existing antiviral antibodies (i.e. antibodies in a naive patient who has not been exposed to the therapeutic virus) or antiviral antibodies induced through previous exposure to the therapeutic virus. The method of the present invention and the materials provided are suitable for use in the clinical environment, particularly in conjunction with the administration of therapeutic products comprising engineered therapeutic viruses.

Whether or not an individual possesses pre-existing neutralizing antibodies to a given virus may be readily determined by conventional assay procedures. Example 2 herein provides an example of such an assay which may readily be employed in the clinical environment. Similar assays relating to the detection of other antiviral antibodies are known in the scientific literature may readily be employed.

Although a subject may not possess antibodies to a given therapeutic virus, following the administration of the first dose of such virus, the immune system of the mammal will mount an immune response against the vector. Consequently, the method of the present invention is particularly useful in the context where multiple doses of the virus are administered to the subject over a prolonged period of time. The fact that the present invention facilitates the re-dosing of an individual with a given therapeutic virus is of particular value.

Apheresis procedures are commonly practiced in the clinical environment and the adjustments to the following general procedure for the individual patient will be readily apparent to the ordinarily skilled clinician. Conventional aseptic technique should be employed throughout the procedure. Certain precautions commonly evaluated in the practice of apheresis procedures should be observed. For example, patients who are receiving angiotensin converting enzyme (ACE) inhibitor medications should not use such medications for a period of approximately 72 hours prior to initiation of the apheresis procedure. Additionally, patients exhibiting significant vascular or intracranial diseases where minor fluid or pressure shifts could result in harmful effects, patients with impaired renal function, severe anemia or systemic infections should be carefully evaluated by the clinician for their suitability for apheresis procedures.

The blood volume of a typical human being is 69 ml/kg of body weight for human males and 65 ml/kg for human females. Of this volume 39 ml/kg (males) and 40 ml/kg (females) is attributable to plasma volume. Consequently a typical male human patient weighing 75 kg possesses a plasma volume of approximately 3 liters. It is not essential that the entire plasma volume of the patient be isolated and subjected to the column procedure in order to achieve a therapeutically significant reduction in the preexisting immunity. A reduction of serum neutralizing titer of approximately one log results in significant increase in transduction efficiency of recombinant adenoviral constructs. A reduction in titer of approximately two logs is more preferred. Additional reductions in serum neutralizing titer are preferable, but are not believed to be clinically necessary. However, it is preferred that a substantial fraction of the plasma volume (1 liter or more) be isolated for treatment. This volume of serum is routinely isolated by conventional apheresis techniques.

Human serum contains a variety of antibodies only a fraction of which are related to neutralizing activity. For example human plasma contains approximately 10 mg/ml of IgG, only a fraction of which is associated with neutralizing anti-adenoviral activity. Consequently, the immunoaffinity chromatographic column preferably comprises approximately 100–500 mg of adenoviral capsid protein or protein G (more preferably 200–400 mg) bound to the chromatographic support per each liter of plasma to be treated. Adenoviral capsid proteins may be obtained by culture of adenoviruses in accordance with known procedures. lmmunoadsorption column supports comprising cross-linked protein G are available from commercial sources such as Zymed Laboratories, Inc., 458 Carlton Court, South San Francisco, Calif. 94080.

Prior to clinical use, the immunoaffinity chromatographic material should be thoroughly washed by passing approximately three bed volumes of clinical sterile phosphate buffered saline through the column. Following the washing procedure, one bed volume of heparin sulfate (approximately 5000 units in a volume 500 ml) should be introduced into the column. The column is then placed upright and should not be agitated or air allowed to enter the column bed or feed lines. A conventional arrangement of the apparatus used in the practice of the method of the present invention is represented schematically in FIG. 9 of the attached drawings.

Venous access to the patient is established and the venous whole blood enters the apheresis apparatus where plasma components are isolated from other non-plasma components. Non-plasma components are returned to the patient's bloodstream. Plasma components are directed to the immunoaffinity chromatographic column. The isolated serum should be passed through the immunoaffinity chromatographic column at a flow rate of from approximately 5 ml/min to approximately 25 ml/min. More preferably, a flow rate of from 10–20 ml/min is maintained throughout the course of the procedure. The first volume equivalent to at least the heparin volume should be discarded to avoid the introduction of heparin to the patient. Remaining column purified serum is directed to the vessel for receiving treated plasma. Prior to reintroduction to the patient, it is preferred that the treated plasma components may be passed through a leukocyte filter (e.g. Pall PL100® filter commercially available from Pall Corporation, 2200 Northern Boulevard, East Hills, N.Y. 11548) to remove microaggregates. Additionally, in order to avoid any air volume entering the line returning to the patient's venous supply, a drip chamber should be employed.

The reduction of serum neutralizing capacity resulting from the present procedure results in a reduction of serum neutralizing capacity persisting for at least 5 days. Consequently, in order to maximize the therapeutic benefit of the foregoing procedure, it is preferred that the administration of the virus should occur within this period of time following the procedure. Since the depletion of antiviral antibodies is observed relatively quickly following the plasmapheresis procedure and the immune system immediately attempts to regenerate this response, it is preferred that the plasmapheresis procedure be performed relatively soon (preferably hours) prior to administration(s) of the therapeutic virus. Additionally, since injection of the therapeutic virus results in a further depleted serum neutralizing antibody, further administrations of virus (serial injection) may be performed from about one hour to about one day after the initial dose to take maximal effect of this secondary antibody depletion. Although the plasmapheresis procedure is well tolerated by human patients there is no technical limitation to daily performance of this procedure to achieve the maximal effect. However, as previously stated, the effect produced is of sufficient duration that daily repetition of the process is not generally required.

It should be noted that it is not essential to completely deplete the antiviral antibodies from the circulation in order to provide a beneficial effect. Consequently, it is not necessary that the entire plasma volume of the individual be subjected to the present chromatographic procedure. Although the effect of the procedure on minimizing immune response to a therapeutic virus is enhanced with increased diminution of the levels of antiviral antibodies, even a relatively modest reduction in the concentration of antiviral antibodies can provide a significant therapeutic effect. In the preferred practice of the invention, in accordance with conventional apheresis procedure, approximately one liter of serum is isolated for purification over the immunoaffinity column in a single procedure. If greater reduction of antiviral antibodies is required, the procedure may be expanded to cope with larger volumes or be performed repeatedly.

The terms "therapeutic virus" and "therapeutic viral vector" are used interchangeably herein to refer to viruses used as therapeutic agents (e.g. wild-type viruses, attenuated viruses), vaccine vectors or recombinant viruses containing modifications to the genome to enhance therapeutic effects. The use of viruses or "viral vectors" as therapeutic agents are well known in the art as previously discussed. Additionally, a number of viruses are commonly used as vectors for the delivery of exogenous genes. Commonly employed vectors include recombinantly modified enveloped or non-enveloped DNA and RNA viruses, preferably selected from baculoviridiae, parvoviridiae, picornoviridiae, herpesveridiae, poxviridae, adenoviridiae, or picomnaviridiae. Chimeric vectors may also be employed which exploit advantageous elements of each of the parent vector properties (See e.g., Feng, et al.(1997) Nature Biotechnology 15:866–870). Such viral vectors may be wild-type or may be modified by recombinant DNA techniques to be replication deficient, conditionally replicating or replication competent.

Therapeutic viruses are currently administered to mammalian subjects by a variety of routes of administration including local administration (e.g. intratumoral injection), regional administration (e.g. intraperitoneal, intravesicular, or intrahepatic arterially) and systemic administration (e.g. intramuscular and intravenous).

Preferred vectors are derived from the adenoviral, adeno-associated viral and retroviral genomes. In the most preferred practice of the invention, the vectors are derived from the human adenovirus genome. Particularly preferred vectors are derived from the human adenovirus serotypes 2 or 5. The replicative capacity of such vectors may be attenuated (to the point of being considered "replication deficient") by modifications or deletions in the E1a and/or E1b coding regions. Other modifications to the viral genome to achieve particular expression characteristics or permit repeat administration or lower immune response are preferred. Most preferred are human adenoviral type 5 vectors containing a DNA sequence encoding the p53 tumor suppressor gene. In the most preferred practice of the invention as exemplified herein, the vector is replication deficient vector adenoviral vector encoding the p53 tumor suppressor gene A/C/N/53 as described in Gregory, et al., U.S. Pat. No. 5,932,210 issued Aug. 3, 1999 (the entire teaching of which is herein incorporated by reference).

Alternatively, the viral vectors may be conditionally replicating or replication competent. Conditionally replicating viral vectors are used to achieve selective expression in particular cell types while avoiding untoward broad spectrum infection. Examples of conditionally replicating vectors are described in Pennisi, E. (1996) Science 274:342–343; Russell, and S. J. (1994) Eur. J. of Cancer 30A(8):1165–1171. Additional examples of selectively replicating vectors include those vectors wherein an gene essential for replication of the virus is under control of a promoter which is active only in a particular cell type or cell state such that in the absence of expression of such gene, the virus will not replicate. Examples of such vectors are described in Henderson, et al., U.S. Pat. No. 5,698,443 issued Dec. 16, 1997 and Henderson, et al., U.S. Pat. No. 5,871,726 issued Feb. 16, 1999 the entire teachings of which are herein incorporated by reference.

Additionally, the viral genome may be modified to include inducible promoters which achieve replication or expression only under certain conditions. Examples of inducible promoters are known in the scientific literature (See, e.g. Yoshida and Hamada (1997) Biochem. Biophys. Res. Comm. 230:426–430; Iida, et al. (1996) J. Virol. 70(9):6054–6059; Hwang, et al.(1997) J. Virol 71(9):7128–7131; Lee, et al. (1997) Mol. Cell. Biol. 17(9):5097–5105; and Dreher, et al.(1997) J. Biol. Chem 272(46); 29364–29371.

The viruses may also be designed to be selectively replicating viruses. Particularly preferred selectively replicating viruses are described in Ramachandra, et al. PCT International Publication No. WO 00/22137, International Application No. PCT/US99/21452 published Apr. 20, 2000 and Howe, J., PCT International Publication No. WO WO0022136, International Application No. PCT/US99/21451 published Apr. 20, 2000. A particularly preferred selectively replicating recombinant adenovirus is the virus dl01/07/309 as more fully described in Howe, J.

It has been demonstrated that viruses which are attenuated for replication are also useful in the therapeutic arena. For example the adenovirus dl1520 containing a specific deletion in the E1b55K gene (Barker and Berk (1987) Virology 156: 107) has been used with therapeutic effect in human beings. Such vectors are also described in McCormick (U.S. Pat. No. 5,677,178 issued Oct. 14, 1997) and McCormick, U.S. Pat. No. 5,846,945 issued Dec. 8, 1998. The method of the present invention may also be used in combination with the administration of such vectors to minimize the pre-existing or induced humoral immune response to such vectors.

Additionally, the therapeutic virus may incorporate a therapeutic transgene for expression in an infected cell. The term "therapeutic transgene" refers to a nucleotide sequence the expression of which in the target cell produces a therapeutic effect. The term therapeutic transgene includes but is not limited to tumor suppressor genes, antigenic genes, cytotoxic genes, cytostatic genes, pro-drug activating genes, apoptotic genes, pharmaceutical genes or anti-angiogenic genes. The vectors of the present invention may be used to produce one or more therapeutic transgenes, either in tandem through the use of IRES elements or through independently regulated promoters.

The term "tumor suppressor gene" refers to a nucleotide sequence, the expression of which in the target cell is capable of suppressing the neoplastic phenotype and/or inducing apoptosis. Examples of tumor suppressor genes useful in the practice of the present invention include the p53 gene, the APC gene, the DPC-4 gene, the BRCA-1 gene, the BRCA-2 gene, the WT-1 gene, the retinoblastoma gene (Lee, et al. (1987) Nature 329:642), the MMAC-1 gene, the adenomatous polyposis coli protein (Albertsen, et al., U.S. Pat. No. 5,783,666 issued Jul. 21, 1998), the deleted in colon carcinoma (DCC) gene, the MMSC-2 gene, the NF-1 gene, nasopharyngeal carcinoma tumor suppressor gene that maps at chromosome 3 p21.3. (Cheng, et al. 1998. Proc. Nat. Acad. Sci. 95:3042–3047), the MTS1 gene, the CDK4 gene, the NF-1 gene, the NF2 gene, and the VHL gene. A particularly preferred adenovirus for therapeutic use is the ACN53 vector encoding the p53 tumor suppressor gene as more fully described in Gregory, et al., U.S. Pat. No. 5,932,210 issued Aug. 3, 1999, the entire teaching of which is herein incorporated by reference.

The term "antigenic genes" refers to a nucleotide sequence, the expression of which in the target cells results in the production of a cell surface antigenic protein capable of recognition by the immune system. Examples of antigenic genes include carcinoembryonic antigen (CEA), p53 (as described in Levine, A. PCT International Publication No. WO94/02167 published Feb. 3, 1994). In order to facilitate immune recognition, the antigenic gene may be fused to the MHC class I antigen.

The term "cytotoxic gene" refers to nucleotide sequence, the expression of which in a cell produces a toxic effect. Examples of such cytotoxic genes include nucleotide sequences encoding pseudomonas exotoxin, ricin toxin, diptheria toxin, and the like.

The term "cytostatic gene" refers to nucleotide sequence, the expression of which in a cell produces an arrest in the cell cycle. Examples of such cytostatic genes include p21, the retinoblastoma gene, the E2 F-Rb gene, genes encoding cyclin dependent kinase inhibitors such as P16, p15, p18 and p19, the growth arrest specific homeobox (GAX) gene as described in Branellec, et al. (PCT Publication WO97/16459 published May 9, 1997 and PCT Publication WO96/30385 published Oct. 3, 1996).

The term "cytokine gene" refers to a nucleotide sequence, the expression of which in a cell produces a cytokine. Examples of such cytokines include GM-CSF, the interleukins, especially IL-1, IL-2, IL-4, IL-12, IL-10, IL-19, IL-20, interferons of the α, β and γ subtypes, consensus interferons and especially interferon α-2 b and fusions such as interferon α-2α-1.

The term "chemokine gene" refers to a nucleotide sequence, the expression of which in a cell produces a cytokine. The term chemokine refers to a group of structurally related lowmolecular cytokines weight factors secreted by cells are structurally related having mitogenic, chemotactic or inflammatory activities. They are primarily cationic proteins of 70 to 100 amino acid residues that share four conserved cysteine. These proteins can be sorted into two groups based on the spacing of the two amino-terminal cysteines. In the first group, the two cysteines are separated by a single residue (C-x-C), while in the second group, they are adjacent (C-C). Examples of member of the 'C-x-C' chemokines include but are not limited to platelet factor 4 (PF4), platelet basic protein (PBP), interleukin-8 (IL-8), melanoma growth stimulatory activity protein (MGSA), macrophage inflammatory protein 2 (MIP-2), mouse Mig (m 119), chicken 9 E3 (or pCEF-4), pig alveolar macrophage chemotactic factors I and II (AMCF-I and -II), pre-B cell growth stimulating factor (PBSF),and IP10. Examples of members of the 'C-C' group include but are not limited to monocyte chemotactic protein 1 (MCP-1), monocyte chemotactic protein 2 (MCP-2), monocyte chemotactic protein 3 (MCP-3), monocyte chemotactic protein 4 (MCP4), macrophage inflammatory protein 1α (MP-1-α), macrophage inflammatory protein 1β (MIP1-β), macrophage inflammatory protein 1-γ (MIP-1-γ), macrophage inflammatory protein 3α (MIP-3-α, macrophage inflammatory protein 3β (MIP-3-β), chemokine (ELC), macrophage inflammatory protein-4 (MIP-4), macrophage inflammatory protein 5 (MIP-5), LD78 β, RANTES, SIS-epsilon (p500), thymus and activation-regulated chemokine (TARC), eotaxin, I-309, human protein HCC-1/NCC-2, human protein HCC-3, mouse protein C10.

The term "pharmaceutical protein gene" refers to nucleotide sequence, the expression of which results in the production of protein have pharmaceutically effect in the target cell. Examples of such pharmaceutical genes include the proinsulin gene and analogs (as described in PCT International Patent Application No. WO98/31397, growth hormone gene, dopamine, serotonin, epidermal growth factor, GABA, ACTH, NGF, VEGF (to increase blood perfusion to target tissue, induce angiogenesis, PCT publication WO98/32859 published Jul. 30, 1998), thrombospondin etc.

The term "pro-apoptotic gene" refers to a nucleotide sequence, the expression thereof results in the induction of the programmed cell death pathway of the cell. Examples of pro-apoptotic genes include p53, adenovirus E3-11.6K (10.5K), the adenovirus E4orf4 gene, p53 pathway genes, and genes encoding the caspases.

The term "pro-drug activating genes" refers to nucleotide sequences, the expression of which, results in the production of protein capable of converting a non-therapeutic compound into a therapeutic compound, which renders the cell susceptible to killing by external factors or causes a toxic condition in the cell. An example of a prodrug activating gene is the cytosine deaminase gene. Cytosine deaminase converts 5-fluorocytosine to 5 fluorouracil, a potent antitumor agent). The lysis of the tumor cell provides a localized burst of cytosine deaminase capable of converting 5 FC to 5 FU at the localized point of the tumor resulting in the killing of many surrounding tumor cells. This results in the killing of a large number of tumor cells without the necessity of infecting these cells with an adenovirus (the so-called bystander effect"). Additionally, the thymidine kinase (TK) gene (see e.g. Woo, et al. U.S. Pat. No. 5,631,236 issued May 20, 1997 and Freeman, et al. U.S. Pat. No. 5,601,818 issued Feb. 11, 1997) in which the cells expressing the TK gene product are susceptible to selective killing by the administration of gancyclovir may be employed.

The term "anti-angiogenic" genes refers to a nucleotide sequence, the expression of which results in the extracellular secretion of anti-angiogenic factors. Anti-angiogenesis factors include angiostatin, inhibitors of vascular endothelial growth factor (VEGF) such as Tie 2 (as described in PNAS(USA)(1998) 95:8795–8800), endostatin.

It will be readily apparent to those of skill in the art that modifications and or deletions to the above referenced genes so as to encode functional subfragments of the wild type protein may be readily adapted for use in the practice of the present invention. For example, the reference to the p53 gene includes not only the wild type protein but also modified p53 proteins. Examples of such modified p53 proteins include modifications to p53 to increase nuclear retention, deletions such as the Δ13–19 amino acids to eliminate the calpain consensus cleavage site (Kubbutat and Vousden (1997) Mol. Cell. Biol. 17:460–468, modifications to the oligomerization domains (as described in Bracco, et al. PCT published application WO97/0492 or U.S. Pat. No. 5,573,925, etc.).

It will be readily apparent to those of skill in the art that the above therapeutic genes may be secreted into the media or localized to particular intracellular locations by inclusion of a targeting moiety such as a signal peptide or nuclear localization signal(NLS). Also included in the definition of therapeutic transgene are fusion proteins of the therapeutic transgene with the herpes simplex virus type 1 (HSV-1) structural protein, VP22. Fusion proteins containing the VP22 signal, when synthesized in an infected cell, are exported out of the infected cell and efficiently enter surrounding non-infected cells to a diameter of approximately 16 cells wide. This system is particularly useful in conjunction with transcriptionally active proteins (e.g. p53) as the fusion proteins are efficiently transported to the nuclei of the surrounding cells. See, e.g. Elliott, G. & O'Hare, P. Cell. 88:223–233:1997; Marshall, A. & Castellino, A. Research News Briefs. Nature Biotechnology. 15:205:1997; O'Hare, et al. PCT publication WO97/05265 published Feb. 13, 1997. A similar targeting moiety derived from the HIV Tat protein is also described in Vives, et al. (1997) J. Biol. Chem. 272:16010–16017.

It may be valuable in some instances to utilize or design vectors to achieve introduction of the exogenous transgene in a particular cell type. Certain vectors exhibit a natural tropism for certain tissue types. For example, vectors derived from the genus herpesviridae have been shown to have preferential infection of neuronal cells. Examples of recombinantly modified herpesviridae vectors are disclosed in U.S. Pat. No. 5,328,688 issued Jul. 12, 1994. Cell type specificity or cell type targeting may also be achieved in vectors derived from viruses having characteristically broad infectivities by the modification of the viral envelope proteins. For example, cell targeting has been achieved with adenovirus vectors by selective modification of the viral genome knob and fiber coding sequences to achieve expression of modified knob and fiber domains having specific interaction with unique cell surface receptors. Examples of such modifications are described in Wickham, et al.(1997) J. Virol 71(11):8221–8229 (incorporation of RGD peptides into adenoviral fiber proteins); Arnberg, et al.(1997) Virology 227:239–244 (modification of adenoviral fiber genes to achieve tropism to the eye and genital tract); Harris and Lemoine (1996) TIG 12(10):400405; Stevenson, et al. (1997) J. Virol. 71(6):4782–4790; Michael, et al.(1995) Gene Therapy 2:660–668 (incorporation of gastrin releasing peptide fragment into adenovirus fiber protein); and Ohno, et al.(1997) Nature Biotechnology 15:763–767 (incorporation of Protein A-IgG binding domain into Sindbis virus). Other methods of cell specific targeting have been achieved by the conjugation of antibodies or antibody fragments to the envelope proteins (see, e.g. Michael, et al. (1993) J. Biol. Chem 268:6866–6869, Watkins, et al. (1997) Gene Therapy 4:1004–1012; Douglas, et al.(I996) Nature Biotechnology 14:1574–1578. Alternatively, particularly moieties may be conjugated to the viral surface to achieve targeting (See, e.g. Nilson, et al. (1996) Gene Therapy 3:280–286 (conjugation of EGF to retroviral proteins)). Additionally, the virally encoded therapeutic transgene also be under control of a tissue specific promoter region allowing expression of the transgene preferentially in particular cell types.

In the preferred practice of the invention, this procedure is employed in conjunction with recombinant adenoviral therapy for the treatment of human cancers. In accordance with conventional oncology practice, patients are dosed at the maximum tolerated dose of the therapeutic agent. In the course of clinical investigation, a dose of $1.5 \times 10^{13}$ recombinant adenoviral particles is well tolerated in human subjects. Clinical experience with replication deficient recombinant adenoviruses expressing p53 has indicated that a course of therapy of injection of approximately $1\times10^{13}$ recombinant viral particles for a period of 5 days repeated weekly for a period of three weeks is effective in the treatment of ovarian cancer in human beings. The therapeutic treatment regimen preferred in the present invention would involve removal of antiviral antibodies using the plasmapheresis technique described above followed by this course of therapy. Moreover, the injection of recombinant adenoviruses in such quantity may further deplete antibodies thus enhancing subsequent transduction.

The following is a description of procedures and parameters for the conventional application of this procedure in conjunction with the administration of a replication deficient recombinant adenovirus encoding p53 ACN53 for the treatment of ovarian cancer. A typical course of therapy with this agent involves administration of $1.5\times10^{13}$ viral particles each day for a period of 5 days. An FDA Phase III approved clinical protocol for the treatment of ovarian cancer using the ACN53 virus calls involves a typical 5 day course of therapy described above in conjunction with the chemotherapeutic agents cisplatin and paclitaxel. Patients receive three courses of therapy with intervening rest periods. Modifications to this procedure for therapeutic viruses other than adenovirus will be readily apparent to the skilled artisan Prior to the initiation of treatment with the therapeutic virus, the patient may optionally be assayed for the presence of pre-existing antiviral antibodies in accordance with standard assay procedures well known in the art. An assay for the determination of antiadenoviral antibodies is provided in Example 3 herein. This pre-screening may be more indicated in the naive patient as the patient who has been previously exposed to the therapeutic virus in previous courses of therapy may generally be assumed to possess such antibodies. In the event that the patient possesses pre-existing or induced neutralizing antibodies, an immunoaffinity chromatographic material comprising 250 mg of adenoviral capsid proteins in a column format is a vessel of 300 ml volume is prepared in substantial accordance with the teaching of Example 2 herein and sterilized for use. The vessel containing the chromatographic material is affixed to a support in an upright fashion. An apparatus as described above is prepared and arranged in substantial accordance with the schematic representation in FIG. 9 of the attached drawings. The column is washed with three bed volumes of sterile phosphate buffered saline. 500 ml of heparin are introduced into the vessel and the excess discarded. Venous blood supply to the apheresis apparatus is established by catheterization of the cephalic vein. The plasma output port of the apheresis apparatus is connected via flexible tubing to the bottom inlet port of the vessel containing the chromatographic material. Plasma is allowed to enter the vessel containing the chromatographic material. Plasma flow should be established initially at approximately 10 ml/min. The first 400 ml of serum emanating from the top of the column should be discarded as it is substantially polluted with heparin. The remaining volume is directed to the holding vessel for reintroduction to the patient. If possible, the plasma flow should be increased to approximately 15–20 ml/min. Following the treatment of approximately 1–1.5 liters of serum, the procedure should be discontinued. If additional volumes are to be treated, a new chromatographic resin should be employed.

Use of Viral Evitopes

The present invention further provides a improved method for treating a mammalian subject with a therapeutic virus, the method comprising administering to said mammal a viral epitope or viral epitope mimetic followed by the administration of a therapeutically effective dose of a therapeutic virus. Alternatively to the plasmapheresis procedure described above to remove the antibodies, one may also administer a quantity of the antiviral epitope into the bloodstream of the mammal to be treated. In some instances, these viral coat proteins are toxic (such as adenoviral hexon and fiber protein) in which case it is preferred to administer a quantity of an epitope mimetic (either peptidyl or small molecule organic compound). These agents are then able to bind up the pre-existing antiviral antibodies in circulation. As described above, the injection of rAd vector will also deplete neutralizing antibody from the serum, and thus is useful for in vivo antibody depletion and redosing. The data presented in FIG. 4 further demonstrates that high affinity antibodies are essentially completely depleted by administration of virus. This indicates that pre-treatment of an individual with the virus will deplete the pre-existing or induced immune response to a virus of that type. Thus administration of a virus or immunological subfragments thereof can reduce pre-existing or induced immune response to a therapeutic virus. This procedure may then be followed by the administration of the therapeutic virus. As shown from the previous data, the duration of immunodepletion is limited. Consequently, it will be preferred to administer this epitope or epitope mimetic relatively soon (within hours) in advance of the therapeutic virus to maximize the efficiency of viral delivery

EXAMPLES

The following examples provide the methodology and results of experiments demonstrating the construction of exemplary hybrid vectors of the invention. It will be apparent to those of skill in the art to which the invention pertains, the present invention may be embodied in forms other than those specifically disclosed in these examples, without departing from the spirit or essential characteristics of the invention. The particular embodiments of the invention described below, are therefore to be considered as illustrative and not restrictive of the scope of the invention. In the following examples, "g" means grams, "ml" means milliliters, "° C." means degrees Centigrade, "min." means minutes, "FBS" means fetal bovine serum.

Example 1

Priming Animals for the Induction of Neutralizing Antibodies in vivo

Figure 1:
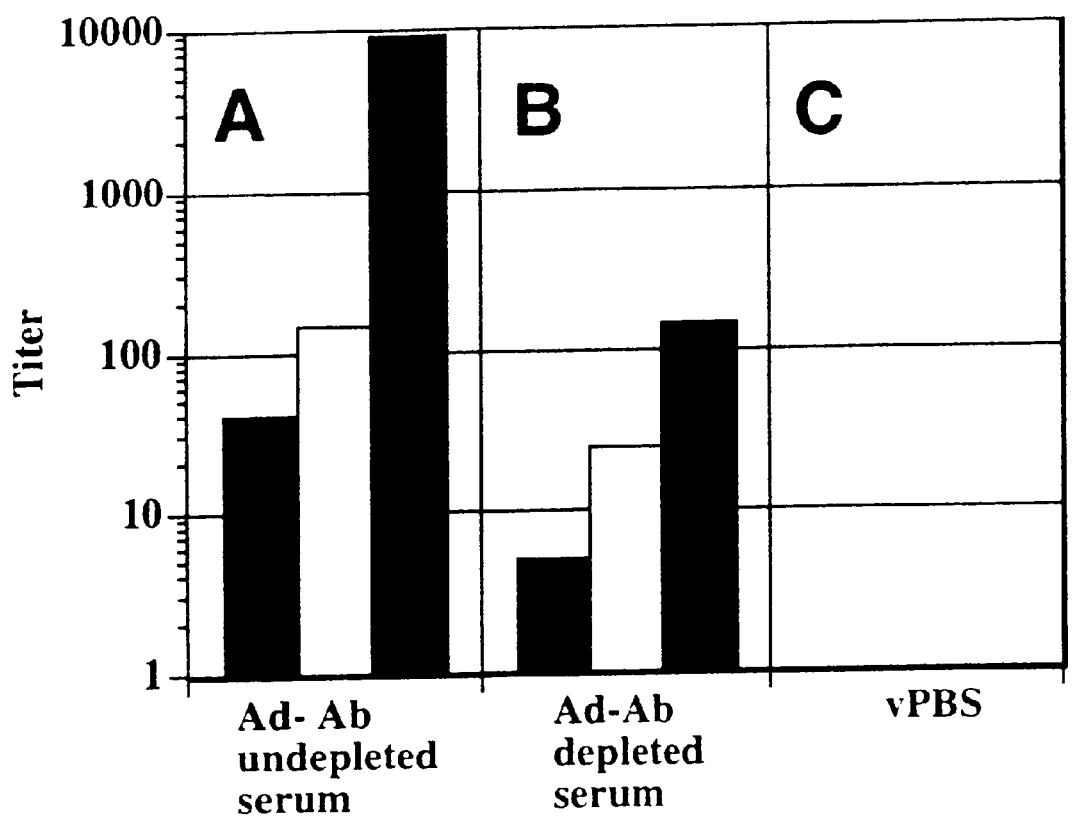
FIG. 1 is a histogram representing ID50 values of anti-adenoviral neutralizing antibodies following subcutaneous administration of adenovirus. The first column (solid black) represents antibody titer observed at 7–10 days following a single adenovirus injection. The second column (white) represents antibody titer observed at 14 days following a single adenovirus injection. The third column (gray) represents antibody titer at 70 days following two subcutaneous injections of recombinant adenovirus. Panel A represents the antibody titer of unpurified serum. Panel B represents antibody titer of serum purified over a column containing adenoviral capsid epitopes. Panel C represents a vPBS control. As can be seen from the data presented, antibody titer is significantly higher following re-dosing (injections, 70 days).

15 BALB/C mice were injected subcutaneously with $5\times10^{10}$ particles of ZZCB. After 28 days, the mice received a booster injection of 5 x 1010 particles subcutaneously. 2 weeks following the second injection, the mice were sacrificed and the serum was isolated. The serum (referred to as Ad-undepleted serum) from all 15 mice were pooled for subsequent experiments. The data is presented in FIG. 1 of the attached drawings. This serum was shown to have a much higher titer than serum from animals that were dosed once with adenovirus. The mice were injected twice with adenovirus to illicit a strong antibody response and mimic a scenario in people pre-exposed to virus and undergoing further therapy with adenovirus.

Example 2

Preparation of the Adenoviral Capsid Protein Column

In order to purify the antibodies from the pooled serum, a chromatography column was prepared in which adenoviral capsid proteins were coupled to Affi-Gel® 15 (commercially available from BioRad as Catalog #1536051). Adenoviral capsid proteins (hexon, penton, fiber and 3A) were purified chromatographically in accordance with the teaching of Shabram, et al. supra. and purified to homogeneity using. Known amounts of hexon (210 µg), penton (522 µg), fiber (146 µg) and 3A (105 µg) were coupled to Affi-Gel® 15 in substantial accordance with the instructions provided by the manufacturer. Coupling efficiency was determined to be approximately 71% by Bradford assay, (as determined by the user). Bradford assay is based on a blue dye (Coomassie Brilliant Blue) that binds to free amino groups in the side chains of amino acids, especially lysine and was performed using a Bio-Rad Protein Assay Kit (commercially available from Bio-Rad) in substantial accordance with the manufacturer's instructions.

Example 3

Purification of Anti-adenoviral Antibodies from Serum of Primed Animals:

200–1500 µl of serum obtained from ZZCB primed animals prepared in substantial accordance with the teaching of Example 1 above was introduced to the column prepared from Example 2. The serum was allowed to bind the adenoviral capsid protein column at four degrees for 2–4 hours with gentle rotation. If less than 1000 µl of serum was used on the column, the serum was diluted to 1000 µl with PBS.

Ad-column adsorbed serum (referred to as column-depleted serum) was collected from the column and anti-adenoviral capsid antibodies (referred to as Ad-Ab) were eluted from the column with 0.2 M glycine pH 2. The antibodies obtained from the column were neutralized in ⅓ volume of 1 M Tris pH8 and then subsequently dialyzed in PBS and stored. The concentration of antibodies depleted from the serum was quantitated by using the Bradford assay.

Figure 2:
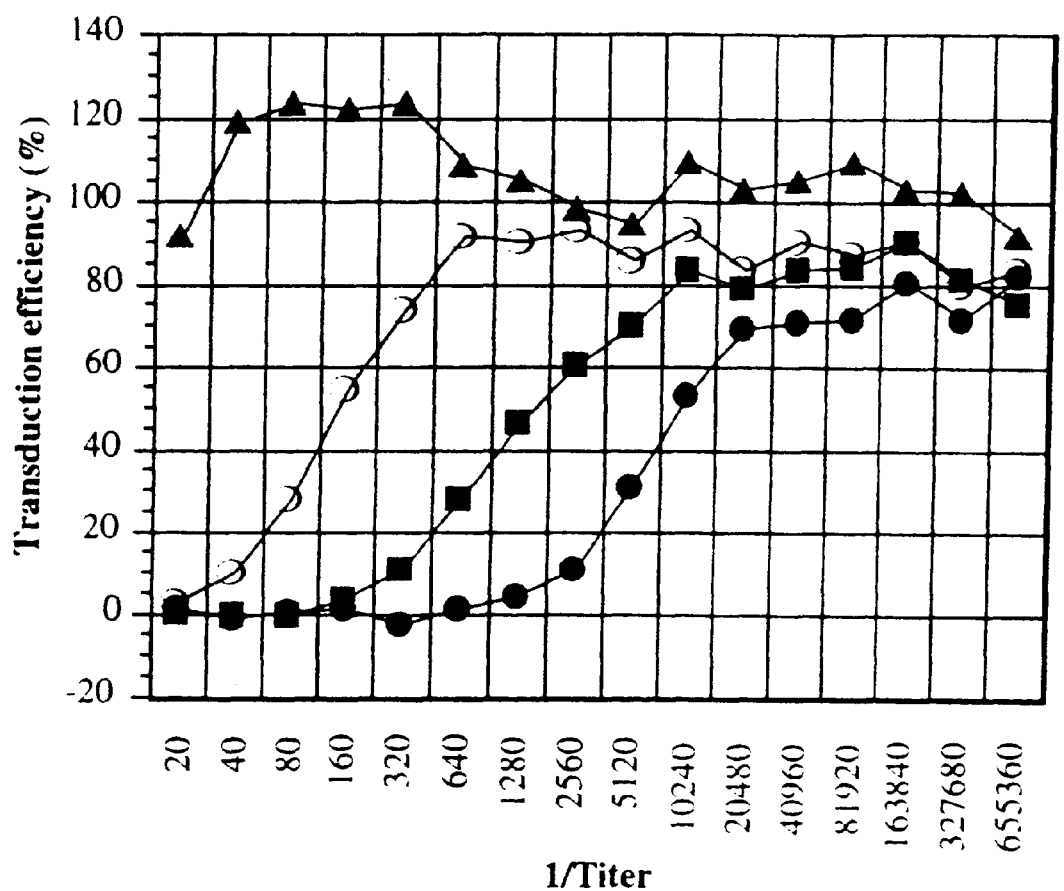
FIG. 2 is a graphical representation of the data demonstrating that removal of anti-adenoviral antibodies results in an increased transduction efficiency of adenovirus in vitro. The vertical axis is a measure of transduction efficiency with rAd/GFP relative to untransduced control HeLa cells. Solid circles represent serum from rAd primed animals. Triangles show transduction efficiently of virus mixed with serum from vPBS injected animals. Open circles indicate serum from rAd primed animals that was depleted of anti-Ad antibodies and squares show transduction efficiency of virus mixed with anti-Ad antibodies, which were eluted from the column used to deplete the anti-Ad antibodies from the rAd primed animals.

In vitro neutralizing assay was performed to show that removal of anti-adenoviral antibodies decreased the neutralizing activity of the serum (FIG. 2). Neutralizing assays were performed by serial dilution of serum of interest (starting at 1:20 dilution and increasing in increments of 2, i.e., 1:40, 1:80, etc.) in a 96 well format. The appropriately diluted serum is allowed to incubate with a recombinant adenovirus (GFCB) expressing the Green Fluorescent Protein (GFP) at a final concentration of $4 \times 10^8$ particles/ml for 1 hr at 37° C. The serum, virus mixture is transferred onto HeLa cells plated at $9 \times 10^3$/well in a 96 well format and the virus is allowed to infect the cells overnight. Fluorescence reading for GFP was evaluated approximately 12 hours later using a fluorometer to assay neutralizing capacity.

Example 4

Gene Transduction in the Absence of Neutralizing Antibodies:

For the experimental procedure to test whether removal of anti-adenoviral antibodies increased the transduction efficiency of virus, 6 mice were passively immunized with either 40 µg of anti-adenoviral antibodies eluted from rAd protein column, or equivalent amounts of column depleted or undepleted serum. An additional 5 mice were passively immunized with serum injected with vPBS and two extra mice were passively immunized with 80 µg of anti-adenoviral antibodies eluted from rAd protein column. Small quantities of sera were collected individually from each mouse 1–3 hours after IP administration to determine if the passive immunization was effective for each particular mouse. The mice were allowed to rest overnight.

Figure 5:
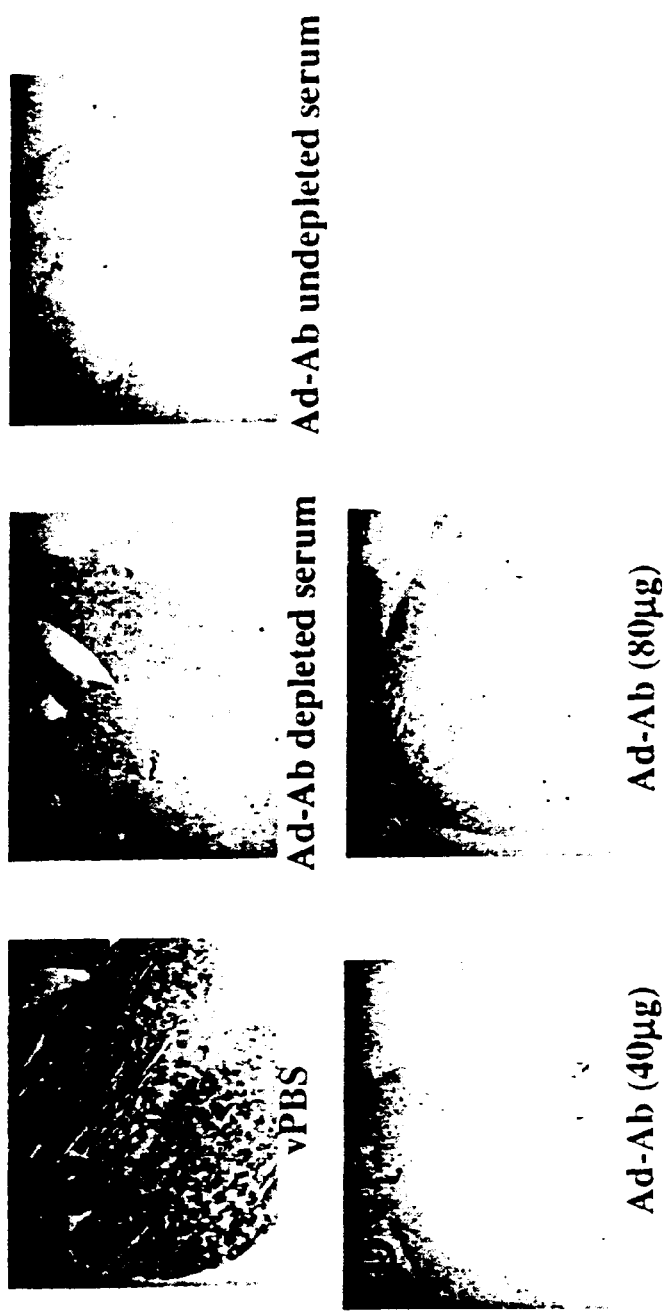
FIG. 5 are photographs of x-gal stained liver cross sections of BALB/c mice following administration with $1 \times 10^{10}$ PN of BGCG. As can be seen with the vPBS control (A), there is substantial staining of the liver due to the absence of a preexisting immune response in mice. Panel B represents the x-gal liver staining of those animal receiving passive immunization of serum depleted of antibodies by passing over an Ad-capsid protein column. Panel C represents β-galactosidase staining of mice receiving passive immunization of unpurified Ad-primed serum. As can be seen from the data presented, a substantial increase in β-galactosidase expression (indicating increased transduction efficiency) was observed in those animals receiving passive immunization of purified serum (B) relative those receiving unpurified serum (C).

The following day, the mice were injected via tail vein injection with $5 \times 10^{10}$ particles of virus (BGCG). BGCG was used so transduction efficiency of the virus could be monitored by staining for β-gal activity in the livers. Two hours following virus injection, the mice were bled a second time to collect serum to observe neutralizing antibody levels. The mice were sacrificed 3 days post virus injection and both serum and livers were isolated from each mouse. The serum was analyzed for neutralizing activity (FIG. 4) and livers were assayed for L-gal activity as an indicator of successful virus transduction (FIG. 5).

We claim:

1. A composition of matter comprising Selective Anti-Viral Immuno-DEpletion (SAVID) immunoaffinity chromatographic material.

2. The composition of claim 1 wherein the SAVID material comprising a viral coat protein linked to a chromatographic support.

3. The composition of claim 2 wherein the viral coat protein is a viral coat protein of an adenovirus.

4. The composition of claim 3 wherein the viral coat protein is a viral coat protein of an adenovirus is selected from the group consisting of hexon, penton, protein IX, protein IIIA fiber, knob and penton base.

* * * * *